United States Patent
Kaislasaari

(10) Patent No.: US 11,160,949 B2
(45) Date of Patent: *Nov. 2, 2021

(54) METHOD, APPARATUS AND COMPUTER PROGRAM PRODUCT FOR PROVIDING A DYNAMIC WAKE-UP ALERT

(71) Applicant: NOKIA TECHNOLOGIES OY, Espoo (FI)

(72) Inventor: Jarkko Kaislasaari, Sunnyvale, CA (US)

(73) Assignee: NOKIA TECHNOLOGIES OY, Espoo (FI)

( * ) Notice: Subject to any disclaimer, the term of this patent is extended or adjusted under 35 U.S.C. 154(b) by 99 days.

This patent is subject to a terminal disclaimer.

(21) Appl. No.: 16/367,317

(22) Filed: Mar. 28, 2019

(65) Prior Publication Data

US 2019/0217047 A1     Jul. 18, 2019

Related U.S. Application Data

(63) Continuation of application No. 15/274,676, filed on Sep. 23, 2016, now Pat. No. 10,245,408.

(51) Int. Cl.
*A61M 21/00* (2006.01)
*A61B 5/00* (2006.01)
(Continued)

(52) U.S. Cl.
CPC .......... *A61M 21/00* (2013.01); *A61B 5/1118* (2013.01); *A61B 5/16* (2013.01); *A61B 5/4815* (2013.01);
(Continued)

(58) Field of Classification Search
None
See application file for complete search history.

(56) References Cited

U.S. PATENT DOCUMENTS 8,666,482 B2 *   3/2014   Wegerif ............. A61B 5/02405
                                                                    600/515
2004/0230398 A1   11/2004   Okada et al.
(Continued)

FOREIGN PATENT DOCUMENTS

CN          103356168 A      10/2013
EP            2701117 A1      2/2014
(Continued)

OTHER PUBLICATIONS

"Assess Your Sleep Needs." [online] [retrieved Nov. 1, 2016] Retrieved from the Internet: <URL: http://healthysleep.med.harvard.edu/need-sleep/what-can-you-do/assess-needs>, 3 pages.
(Continued)

*Primary Examiner* — Kaylee R Wilson
(74) *Attorney, Agent, or Firm* — Alston & Bird LLP

(57) ABSTRACT

A method, apparatus, and computer program product are provided for providing a dynamic wake-up alert. A user's sleep recovery need is determined based on a variety of factors, including but not limited to, mental stress level, physical activity, the individual's sleep history record, and/or data relating to circadian rhythms, recommended sleep times, patterns and cycles. Real-time sleep data, such as that detected by a sleep data detection device, is monitored to determine a real-time gained recovery. Biological, physiological, and/or neurological data relating to the quality of sleep, and/or the amount of sleep obtained is used to calculate the real-time gained sleep recovery of the user and compare the gained recovery to the sleep recovery need. Once the sleep recovery need is satisfied, a dynamic wake-up alert is provided via a user interface.

19 Claims, 2 Drawing Sheets

(51) Int. Cl.
*G16H 50/20* (2018.01)
*G16H 20/30* (2018.01)
*G16H 40/63* (2018.01)
*A61B 5/11* (2006.01)
*A61B 5/16* (2006.01)
*A61B 5/0533* (2021.01)
*A61B 5/024* (2006.01)
*A61B 5/318* (2021.01)
*A61B 5/369* (2021.01)

(52) U.S. Cl.
CPC ............ *A61B 5/7282* (2013.01); *A61B 5/742* (2013.01); *G16H 20/30* (2018.01); *G16H 40/63* (2018.01); *G16H 50/20* (2018.01); *A61B 5/024* (2013.01); *A61B 5/02405* (2013.01); *A61B 5/0533* (2013.01); *A61B 5/165* (2013.01); *A61B 5/318* (2021.01); *A61B 5/369* (2021.01); *A61B 5/4806* (2013.01); *A61M 2021/0022* (2013.01); *A61M 2021/0027* (2013.01); *A61M 2021/0044* (2013.01); *A61M 2021/0083* (2013.01); *A61M 2205/505* (2013.01); *A61M 2205/52* (2013.01); *A61M 2230/04* (2013.01); *A61M 2230/10* (2013.01); *A61M 2230/65* (2013.01)

(56) References Cited

U.S. PATENT DOCUMENTS

| | | | |
|---|---|---|---|
| 2005/0080344 A1* | 4/2005 | Nishii | A61B 5/04 600/483 |
| 2006/0224047 A1 | 10/2006 | Suzuki et al. | |
| 2010/0152546 A1 | 6/2010 | Behan et al. | |
| 2011/0190645 A1* | 8/2011 | Hunt | A61B 5/4833 600/500 |
| 2011/0230790 A1 | 9/2011 | Kozlov | |
| 2011/0267196 A1 | 11/2011 | Hu et al. | |
| 2011/0291842 A1 | 12/2011 | Oexman et al. | |
| 2012/0253220 A1 | 10/2012 | Rai et al. | |
| 2013/0261404 A1 | 10/2013 | Sato et al. | |
| 2014/0073486 A1 | 3/2014 | Ahmed et al. | |
| 2014/0156228 A1 | 6/2014 | Molettiere et al. | |
| 2014/0171146 A1 | 6/2014 | Ma et al. | |
| 2015/0057560 A1 | 2/2015 | Behan et al. | |
| 2015/0127265 A1 | 5/2015 | Iizuka | |
| 2015/0251074 A1* | 9/2015 | Ahmed | A61B 5/02416 700/91 |
| 2015/0348390 A1 | 12/2015 | Berezhnyy et al. | |
| 2016/0022202 A1 | 1/2016 | Peterson et al. | |
| 2016/0246259 A1 | 8/2016 | Zhang | |
| 2017/0127967 A1* | 5/2017 | Garcia Molina | A61B 5/743 |

FOREIGN PATENT DOCUMENTS

| | | |
|---|---|---|
| WO | 2015054134 A1 | 4/2015 |
| WO | 2016001800 A1 | 1/2016 |

OTHER PUBLICATIONS

"Embrace: Monitor Stress, Seizures, Activity, Sleep." [online] [retrieved Nov. 1, 2016] Retrieved from the Internet: <URL: https://www.empatica.com/product-embrace>, 6 pages.
"Sleep." [online] [retrieved Nov. 1, 2016] Retrieved from the Internet: <URL: http://robbwolf.com/category/sleep/>, 6 pages.
Haslam, Chris. "Counting Sheep: The Best Sleep Trackers and Monitors." [online] [retrieved Nov. 1, 2016], Retrieved from the Internet: <URL: http://www.wareable.com/withings/best-sleep-trackers-and-monitors>, 21 pages.
Israel, B. et al. "Short-Term Stability of Sleep and Heart Rate Variability in Good Sleepers and Patients with Insomnia: For Some Measures, One Night is Enough." Sleep, vol. 25, No. 9, 2012, pp. 1285-1291.
Johannes, Lauren. "Smart Alarms Decide When You Should Really Wake Up." Wall Street Journal, Apr. 23, 2012. [online] [retrieved Nov. 1, 2016] Retrieved from the Internet: <URL: http://www.wsj.com/articles/SB10001424052702303592404577631962413693708>, 5 pages.
Wolf, Robb. "How We Are Wired to Sleep—Part 2." [online] [retrieved Nov. 1, 2016] Retrieved from the Internet: <URL: http://robbwolf.com/2015/06/16/how-we-are-wired-to-sleep-part-2>, 16 pages.
International Search Report and Written Opinion of International Searching Authority for International Patent Application No. PCT/F12017/050648 dated Nov. 24, 2017, 14 pages.
Extended European Search Report for European Patent Application No. 17852473.2 dated Apr. 29, 2020, 8 pages.
Final Office Action for U.S. Appl. No. 15/274,676 dated Aug. 24, 2018.
Non-Final Office Action for U.S. Appl. No. 15/274,676 dated Jan. 30, 2018.
Notice of Allowance for U.S. Appl. No. 15/274,676 dated Nov. 21, 2018.
Office Action for Chinese Application No. 201780069136.X dated Apr. 13, 2021, 8 pages.

* cited by examiner

METHOD, APPARATUS AND COMPUTER PROGRAM PRODUCT FOR PROVIDING A DYNAMIC WAKE-UP ALERT

CROSS REFERENCES TO RELATED APPLICATIONS

This application claims the benefit of priority to U.S. application Ser. No. 15/274,676, filed Sep. 23, 2016 and titled, "A METHOD, APPARATUS AND COMPUTER PROGRAM PRODUCT FOR PROVIDING A DYNAMIC WAKE-UP ALERT," and is hereby incorporated by reference in its entirety.

TECHNOLOGICAL FIELD

An example embodiment of the present invention relates generally to analyzing physical recovery, and more particularly, to a method, apparatus and computer program product for providing a dynamic recovery alert.

BACKGROUND

Many people set alarms to be awoken from their sleep, such as on a nightly basis before going to bed. Some use a repeated scheduled alarm to be sounded at a specified time every day or every weekday. Individuals may set their device alarms according to appointment times or a work start time, for example, without any regard to the amount of sleep that is recommended or needed for healthy recovery. In many cases, an individual is awoken from their sleep without having achieved the optimal amount of sleep recommended for healthy well-being. In some instances, setting an alarm based on a predefined schedule may cause people to sleep longer than what is needed or recommended, thus wasting valuable time that could be spent on other tasks, or detrimentally impacting their ability to sleep in the near future. However, it may be difficult for humans in modern life to define or measure how much one should sleep to fully recover.

BRIEF SUMMARY

A method, apparatus, and computer program product are therefore provided for providing a dynamic wake-up alert. In this regard, the alarm is variable such that the user is awoken once the user's sleep recovery need is satisfied.

Many individuals may find it difficult to determine how much sleep is needed to recover from mental stress, work, errands, daily activities, and exercise. It is also difficult for individuals to understand the quality of past sleep. Some people may forget the details and it is difficult to put a number on personal sleep deprivation or quality at a given time based on a period spanning the past several weeks. Furthermore, certain habits like drinking alcohol, eating a big meal, and exercising late in the day may interfere with the quality of the sleep and thereby minimize its recovery effect. Furthermore, recovery gained during sleep may vary from person to person and on different nights.

Some example embodiments may determine a person's sleep recovery need based on a variety of factors, including but not limited to, a mental stress level, physical stress level, daytime recovery, the individual's sleep history record, and/or data relating to circadian rhythms, autonomic nervous system activity, biological, physiological, and/or neurological data, recommended sleep times, patterns and cycles. Certain example embodiments may therefore determine a personalized sleep recovery need of a user according to any of the aforementioned factors.

During the sleep of the user, some example embodiments may monitor sleep data relating to the user, such as that detected by a sleep data detection device, or any other device and/or sensors, to determine a real-time gained recovery. For example, certain example embodiments may utilize biological, physiological, and/or neurological data relating to the quality of sleep, and/or the amount of sleep obtained, to calculate the real-time actual sleep recovery of the user. The data may be monitored on a repeated or continual basis, such that the real-time gained recovery is compared to the sleep recovery need of the user.

In some examples, the user may only be awoken once the sleep recovery need is satisfied according to the real-time gained recovery. In this regard, some example embodiments provide a dynamic wake-up alert via a user interface.

A method is provided, including determining a sleep recovery need of a user. The method further includes, in response to a sleep event indication, monitoring with a processor, sleep data relating to the user to calculate a real-time gained recovery. The method includes comparing the real-time gained recovery to the determined sleep recovery need, and in response to determining that the real-time gained recovery satisfies the sleep recovery need, causing a wake-up alert to be provided via a user interface of a device.

In some examples, the sleep recovery need is determined based on user-related data received prior to the sleep event. The user-related data received prior to the sleep event may include data relating to a mental stress level of the user, and/or data relating to physical activities of the user. In some examples, the sleep recovery need is determined based on a sleep history record relating to the user. In some examples, the detected sleep data is indicative of a quality of sleep and/or amount of sleep.

In some examples, the method further includes receiving a user input indicative of a desired recovery, and adjusting the determined sleep recovery need based on the desired recovery.

An apparatus is provided comprising at least one processor and at least one memory including computer program code with the at least one memory and the computer program code configured to, with the processor, cause the apparatus to at least determine a sleep recovery need of a user. In some examples, the at least one memory and the computer program code are further configured to, with the processor, cause the apparatus to, in response to a sleep event indication, monitor sleep data relating to the user to calculate a real-time gained recovery. The at least one memory and the computer program code are further configured to cause the apparatus to compare the real-time gained recovery to the determined sleep recovery need, and in response to determining that the real-time gained recovery satisfies the sleep recovery need, cause a wake-up alert to be provided via a user interface of a device.

In some embodiments, the at least one memory and the computer program code may be further configured to receive a user input indicative of a desired recovery, and adjust the determined sleep recovery need based on the desired recovery.

A computer program product is provided comprising at least one non-transitory computer-readable storage medium having computer-executable program code instructions stored therein with the computer-executable program code instructions comprising program code instructions to at least, determine a sleep recovery need of a user, and in response to a sleep event indication, monitoring sleep data relating to the user to calculate a real-time gained recovery. In some examples, the computer-executable program code instructions further comprise program code instructions to compare the real-time gained recovery to the determined sleep recovery need, and in response to determining that the real-time gained recovery satisfies the sleep recovery need, cause a wake-up alert to be provided via a user interface of a device.

An apparatus is provided comprising means for determining a sleep recovery need of a user, and means for, in response to a sleep event indication, monitoring sleep data relating to the user to calculate a real-time gained recovery. The apparatus further includes means for comparing the real-time gained recovery to the determined sleep recovery need. The apparatus further includes means for, in response to determining that the real-time gained recovery satisfies the sleep recovery need, causing a wake-up alert to be provided via a user interface of a device.

BRIEF DESCRIPTION OF THE DRAWINGS

Figure 1:
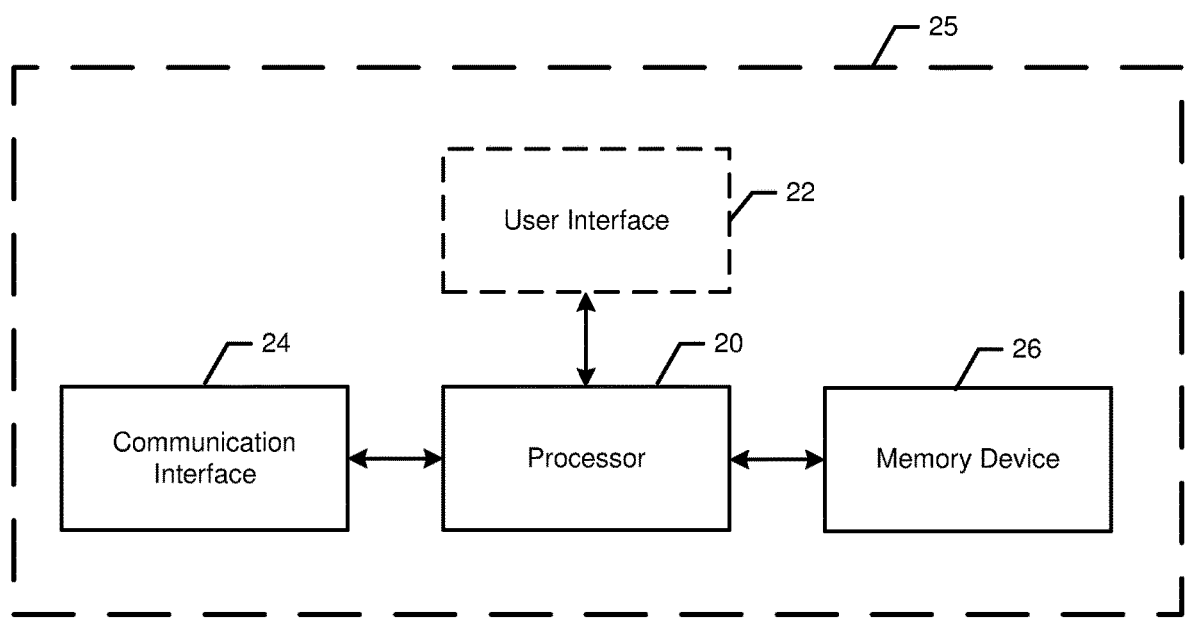
Figure 2:
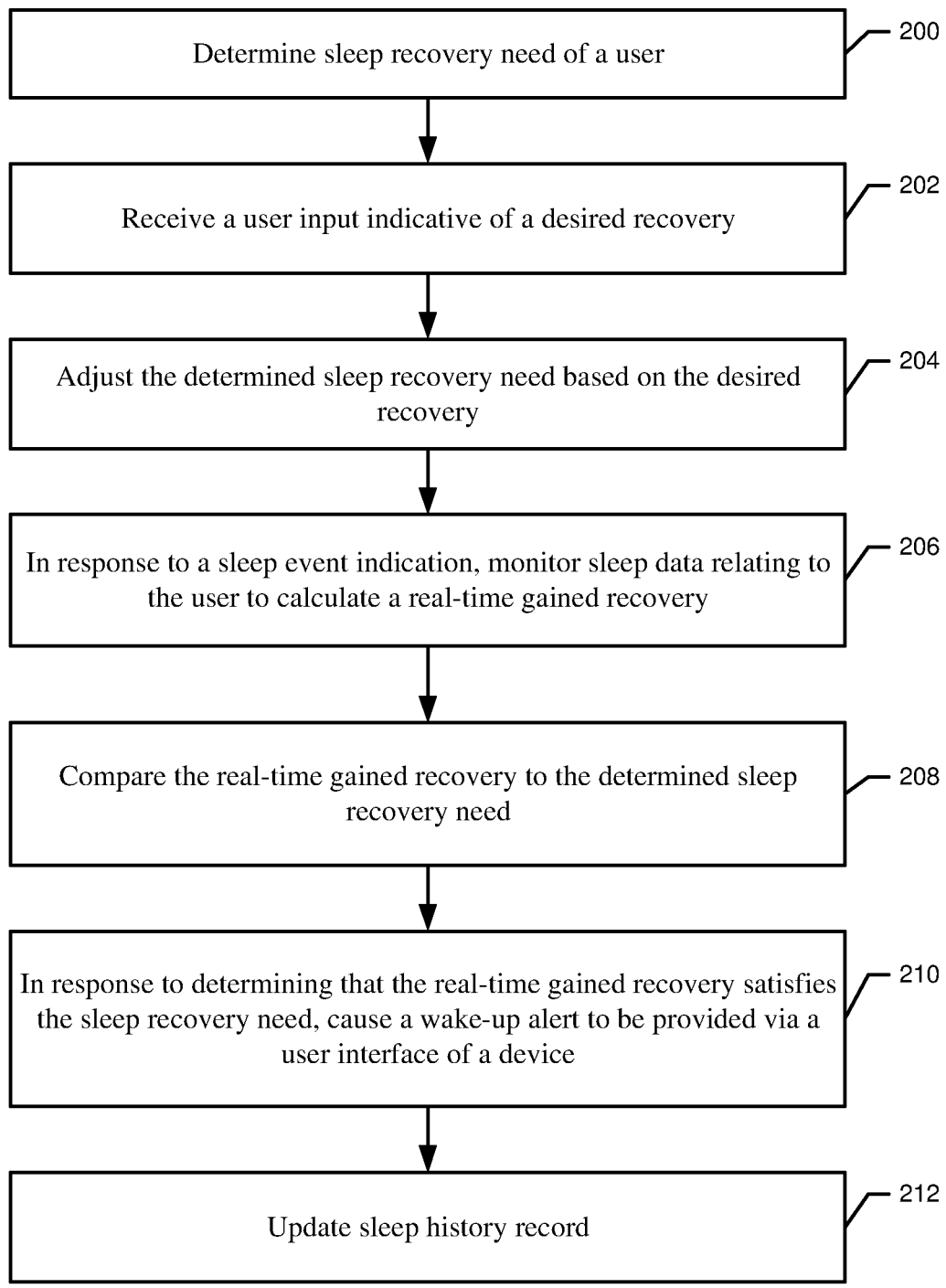

Having thus described certain example embodiments of the present invention in general terms, reference will hereinafter be made to the accompanying drawings which are not necessarily drawn to scale, and wherein:

FIG. 1 is a block diagram of an apparatus that may be configured to implement an example embodiment of the present invention; and FIG. 2 is a flowchart illustrating operations performed in accordance with an example embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device, field programmable gate array, and/or other computing device.

As defined herein, a "computer-readable storage medium," which refers to a physical storage medium (e.g., volatile or non-volatile memory device), may be differentiated from a "computer-readable transmission medium," which refers to an electromagnetic signal.

As described below, a method, apparatus and computer program product are provided for causing a dynamic wake-up alert to be provided via a user interface.

Referring to FIG. 1, apparatus 25 for causing a dynamic wake-up alert to be provided may include or otherwise be in communication with a processor 20, communication interface 24, and memory device 26. As described below and as indicated by the dashed lines in FIG. 1, in some embodiments, the apparatus 25 may also optionally include a user interface 22.

In some examples, apparatus 25 may be implemented as a server or distributed system for causing a dynamic wake-up alert to be provided on a user interface, which may, in some examples, include a user interface of another device. In some examples, apparatus 25 need not necessarily be embodied by a server, and may be embodied by a wide variety of devices including personal computers, work stations, or mobile terminals, such as laptop computers, tablet computers, smartphones, wearable devices or any combination of the aforementioned, and other types of voice and text communications systems. In some examples, apparatus 25 may be embodied by a user device configured to provide the wake-up alert (e.g., auditory alert, vibration, etc.) to a user. Additionally or alternatively, apparatus 25 may be embodied by a sleep data detection device configured to detect, collect and/or monitor data regarding a user's sleep patterns.

In some embodiments, the processor 20 (and/or co-processors or any other processing circuitry assisting or otherwise associated with the processor 20) may be in communication with the memory device 26 via a bus for passing information among components of the apparatus 25. The memory device 26 may include, for example, one or more volatile and/or non-volatile memories. In other words, for example, the memory device 26 may be an electronic storage device (e.g., a computer readable storage medium) comprising gates configured to store data (e.g., bits) that may be retrievable by a machine (e.g., a computing device like the processor 20). The memory device 26 may be configured to store information, data, content, applications, instructions, or the like for enabling the apparatus to carry out various functions in accordance with an example embodiment of the present invention. For example, the memory device 26 could be configured to buffer input data for processing by the processor 20. Additionally or alternatively, the memory device 26 could be configured to store instructions for execution by the processor 20. In some embodiments, the memory device 26 may be configured to store sleep history records, real-time or near real-time sleep data, data regarding physical activity and/or mental stress, and/or other data relating to a user according to example embodiments provided herein.

In some embodiments, the apparatus 25 may be embodied as a chip or chip set. In other words, the apparatus 25 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus 25 may therefore, in some cases, be configured to implement an embodiment of the present invention on a single chip or as a single "system on a chip." As such, in some cases, a chip or chipset may constitute means for performing one or more operations for providing the functionalities described herein.

The processor 20 may be embodied in a number of different ways. For example, the processor 20 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor 20 may include one or more processing cores configured to perform independently. A multi-core processor may enable multiprocessing within a single physical package. Additionally or alternatively, the processor 20 may include one or more processors configured in tandem via the bus to enable independent execution of instructions, pipelining and/or multithreading.

In an example embodiment, the processor 20 may be configured to execute instructions stored in the memory device 26 or otherwise accessible to the processor 20. Alternatively or additionally, the processor 20 may be configured to execute hard coded functionality. As such, whether configured by hardware or software methods, or by a combination thereof, the processor 20 may represent an entity (e.g., physically embodied in circuitry) capable of performing operations according to an embodiment of the present invention while configured accordingly. Thus, for example, when the processor 20 is embodied as an ASIC, FPGA or the like, the processor 20 may be specifically configured hardware for conducting the operations described herein. Alternatively, as another example, when the processor 20 is embodied as an executor of software instructions, the instructions may specifically configure the processor 20 to perform the algorithms and/or operations described herein when the instructions are executed. However, in some cases, the processor 20 may be a processor of a specific device (e.g., a mobile terminal or network entity) configured to employ an embodiment of the present invention by further configuration of the processor 20 by instructions for performing the algorithms and/or operations described herein. The processor 20 may include, among other things, a clock, an arithmetic logic unit (ALU) and logic gates configured to support operation of the processor 20.

Meanwhile, the communication interface 24 may be any means such as a device or circuitry embodied in either hardware or a combination of hardware and software that is configured to receive and/or transmit data from/to a network and/or any other device or module in communication with the apparatus 25. In this regard, the communication interface 24 may include, for example, an antenna (or multiple antennas) and supporting hardware and/or software for enabling communications with a wireless communication network. Additionally or alternatively, the communication interface 24 may include the circuitry for interacting with the antenna(s) to cause transmission of signals via the antenna(s) or to handle receipt of signals received via the antenna(s). In some environments, the communication interface 24 may alternatively or also support wired communication. As such, for example, the communication interface 24 may include a communication modem and/or other hardware/software for supporting communication via cable, digital subscriber line (DSL), universal serial bus (USB) or other mechanisms. The communication interface 24 may be configured to facilitate communication between apparatus 25 and a user device, such as by enabling processor 20 to cause a wake-up alert to be provided via a user interface, such as user interface 22.

In some embodiments, such as instances in which the apparatus 25 is embodied by a user device, the apparatus 25 may include a user interface 22 that may, in turn, be in communication with the processor 20 to receive an indication of a user input and/or to cause provision of an audible, visual, mechanical or other output to the user. As such, the user interface 22 may include, for example, a keyboard, a mouse, a joystick, a display, a touch screen(s), touch areas, soft keys, a microphone, a speaker, or other input/output mechanisms. Alternatively or additionally, the processor 20 may comprise user interface circuitry configured to control at least some functions of one or more user interface elements such as, for example, a speaker, ringer, microphone, display, and/or the like. The processor 20 and/or user interface circuitry comprising the processor 20 may be configured to control one or more functions of one or more user interface elements through computer program instructions (e.g., software and/or firmware) stored on a memory accessible to the processor 20 (e.g., memory device 26, and/or the like). As described in further detail herein, the user interface 22 may be configured for receiving information from a user regarding desired sleep recovery and/or providing a wake-up alert to a user. In some examples, user interface 22 may be embodied by a user device that is remote from or external to apparatus 25.

FIG. 2 is a flowchart of operations performed by apparatus 25 according to an example embodiment. As shown by operation 200, apparatus 25 may include means, such as the processor 20, memory device 26, or the like, for determining a sleep recovery need of a user. The sleep recovery need may include any data describing the sleep needs of a user, such as data describing optimal or ideal sleep quality and/or sleep amounts (e.g., length and/or duration).

Sleep quality may be determined based on predefined guidelines as may be stored on memory device 26, for example. As an example, in an instance sleep data meets or satisfies a threshold of any predefined biological, physiological, and/or neurological measurement, such as those described herein, apparatus 25 may attribute the sleep to a high quality sleep or low quality sleep. In some examples, a sleep quality score may be determined according to any biological, physiological and/or neurological measurement. In some examples, the sleep recovery need may be an overall target score or rating of sleep quality and/or amount, based on a set of guidelines and calculations indicating that relatively higher quality sleep may be weighted more greatly than relatively lower quality sleep, and the duration of sleep attributed to respective sleep qualities is further considered. For example, a sleep recovery need may include 6 hours of high quality sleep or 8 hours of medium quality sleep. It will be appreciated that any classification or scoring of quality may be used, and any reference to low, medium, and/or high quality is provided merely as an example.

The quality and/or amounts of sleep needed may be tailored for a particular user as described herein to determine a sleep recovery need of the user. The sleep recovery need of a user, such as the recommended sleep quality and/or amounts for the user, may be determined based on any of a variety of factors described in further detail hereinafter, including but not limited to, baseline sleep recommendations according to a user demographic information, user-related data received prior to the sleep event, (e.g., data indicative of mental stress and/or physical stress of the user), a sleep history record, and/or the like.

For example, apparatus 25, such as the processor 20, may determine and/or receive baseline sleep recommendations based on age, gender, health conditions, and/or any other information relating to the user. The baseline sleep recommendations may include, for example, a minimum amount of sleep, maximum amount of sleep, and/or a range of amount of sleep per unit of time, such as a per day or per week basis. The baseline sleep recommendations may further include more detail data relating to sleep cycles and the amount of time recommended in each respective cycle. The recommendations may be targeted based on any of the above mentioned information relating to the user as provided by standard medical or sleep guidelines. For example, the baseline sleep recommendations may be accessed on memory device 26.

Apparatus 25, such as the processor 20, may determine an individual or personalized sleep recovery need of a user by adjusting baseline sleep recommendations according to user-related data received prior to a sleep event, such as in the day prior to or a predefined number of days leading up to the sleep event.

The user-related data received prior to the sleep event may include any information relating to mental or physical activities of the user, and may be collected by any number of devices or sensors, such as those attached or implanted to the user and/or in the vicinity of the user. For example, apparatus 25, such as the processor 20 and/or the communication interface 24, may receive data from a wearable device (e.g., step counter or other fitness tracking device) regarding the physical activities of a user. In some examples, an accelerometer, such as one implemented in a user device may provide data regarding the physical activities of the user. In some examples, apparatus 25, such as the processor 20 and/or the communication interface 24, may receive the user-related data relating to physical activity and/or mental stress from any type of sensor or monitor, such as a heart rate monitor (e.g. a photoplethysmogram (PPG) sensor and/or electrocardiography (ECG) sensors), brain activity monitor (e.g. electroencephalogram (EEG)), galvanic skin response detectors, other biological, physiological and/or neurological sensors, and/or the like. As another example, the user-related data may be provided by the user via a user interface, such as by logging activities or stress levels.

For example, apparatus 25, such as the processor 20 and/or the communication interface 24, may receive information indicating or determine that the user has participated in an exceptionally high level of physical activity (e.g., based on a physical activity score, or other measurable indication of physical activity). In this regard, apparatus 25, such as the processor 20, may adjust upwards the baseline recommended sleep needs of the user to determine a sleep recovery need of the user. As another example, on days of little or no physical activity (e.g., low physical activity score), the baseline recommended sleep may be decreased to determine a sleep recovery need of a user.

In some examples, apparatus 25, such as the processor 20, may determine a sleep recovery need of the user based on mental stress indicators. For example, a mental stress indicator may be provided by the user via a user interface. As another example, apparatus 25, such as the processor 20, may access a calendar application of a user and determine a mental stress level reflected in the schedule of the user. In some examples, sensors configured to detect biological, physiological and/or neurological data may be used to determine mental stress.

Apparatus 25, such as the processor 20, may therefore determine the sleep recovery need of the user by adjusting baseline sleep recommendation according to an indicator (e.g., quantitative) of physical activity and/or mental stress. In some examples, the physical activities and/or mental stress levels may be determined cumulatively over a period of time, such as over a week long span, or several weeks.

In some embodiments, apparatus 25, such as the processor 20 and/or the memory device 26, may determine the sleep recovery need of the user further based on a sleep history record of the user. The sleep history record may be accessed on memory device 26, for example, and may include sleep data relating to the user for any predetermined amount of time. For example, the sleep history record may include sleep data detected from the user going back one week, or several weeks. In some examples, accessing a sleep history record of the prior four weeks may be beneficial. In this regard, the sleep recovery need of the user may be based on recent cumulative sleep. The sleep history record may be based on or may comprise offset information, such as data indicating the offset or difference between respective sleep recovery needs and actual gained recovery from the past. In some examples, apparatus 25 may receive sleep data on an ongoing basis, and accumulate the sleep data in the sleep history record of the user.

In some embodiments, the sleep history record may comprise a quantitative sleep deficit, such as a number of hours. In some examples, apparatus 25, such as with processor 20, may calculate a sleep history score indicative of a sleep debt (e.g., deficit) or sleep surplus. The sleep history score may be included in the sleep history record. The sleep recovery need of the user may therefore be determined based on at least on the sleep history record. For example, the baseline sleep recommendation may be adjusted according to the sleep history score and/or sleep history record to determine an individual's sleep recovery need.

In some examples, operation 200 may be modified to determine a physical recovery need of a user, which may be indicative of physical rest (which may or may not be sleep) needed to recover from physical activity.

In operation 202, apparatus 25 may include means, such as the processor 20, user interface 22, communication interface 24, memory device 26, or the like, for receiving a user input indicative of a desired recovery. For example, a user may configure the desired amounts of respective sleep attributed to particular sleep quality or cycle. As another example, a user may input a target percentage or ratio of the determined sleep recovery need that the user desires to achieve. In this regard, when a user feels they need to be awoken earlier than is needed to achieve all of their daily tasks, the user may indicate that only 90%, for example, of the sleep recovery need is desired. As another example, when a user expects that subsequent nights will result in little sleep, the user may wish to obtain 110% of the sleep recovery need.

As shown in operation 212, apparatus 25 may include means, such as the processor 20, memory device 26, or the like, for adjusting the determined sleep recovery need based on the desired recovery. In this regard, the sleep recovery need determined with respect to operation 200 may be adjusted according to the user input of the desired recovery. It will be appreciated that operations 202 and 204 are optional, and according to an example embodiment, the sleep recovery need of the user may not be adjusted based on user input, and instead may be calculated according to operation 200.

Continuing to operation 206, apparatus 25 may include means, such as the processor 20, memory device 26, or the like, for in response to a sleep event indication, monitoring sleep data relating to the user to calculate a real-time gained recovery.

As another example, sleep may be detected by any other sleep data detection device, sensor or system such as those configured to monitor sleep, such that the apparatus 25, such as the processor 20 and/or the communication interface 24, receives a sleep event indication. In some examples, a user may manually indicate sleep onset, such as with a user interface of a user device, prior to falling asleep or going to bed. As another example, a sleep data detection device may include a motion detector, radar detection device, neurological sensors, electrical pulse sensor, any other sleep monitor device, vital sign monitoring device, and/or the like. For example, any such device that detects heart rate, respiration rates, neurological activity, muscle relaxation, periods of rapid eye movement (REM) and non-REM sleep may be considered as a sleep data detection device. As another example, a sleep data detection device may include a user device equipped with an accelerometer, to determine when a user goes to sleep, and/or wakes based on movement and/or user behavior.

The sleep data detection device may be further configured to determine a quality of detected sleep. For example, the data may indicate a scored rating of the sleep quality, or may be classified as high or low quality according to the detected data. For instance, a similar classification or scoring method for determining sleep quality as indicated by baseline information and/or the sleep recovery need may be applied to actual sleep data. It will be appreciated that the sleep event indication may be any data received by the apparatus 25 indicative of the user having fallen asleep or gone to bed.

In an instance in which apparatus 25, such as the processor 20, determines the user is sleeping, the apparatus 25 may continually or repeatedly monitor sleep data to calculate a real-time gained recovery. For example, apparatus 25, such as with processor 20, may process sleep data on a repeated time interval, such as every thirty seconds. The sleep data monitored by apparatus 25 may be detected by apparatus 25, or by any sleep data detection device. In this regard, apparatus 25, such as the processor 20, may access sleep data stored to memory device 26.

The apparatus 25, such as the processor 20, may monitor and process the sleep data to determine a real-time gained recovery by the user. For example, apparatus 25, such as the processor 20, may determine and continually update the quality and/or amount of sleep. For example, the apparatus 25, such as the processor 20 and/or the memory device 26, may accumulate the total amount of predetermined types of sleep or sleep attributed to a specified quality or sleep cycle. For example, apparatus 25, such as the processor 20, may track total minutes of sleep in REM and non-REM cycles to track a real-time gained recovery. In some embodiments, heart rate may be used to determine sleep quality. The apparatus 25, such as the processor 20, may determine that high quality sleep is achieved in times in which the heart rate is relatively low in comparison to a threshold or predefined heart rate, and/or apparatus 25, such as the processor 20, may determine that low quality sleep is achieved in times in which the heart rate is relatively high in comparison to a threshold or predefined heart rate. In some examples, the sleep quality may be determined based on heart rate variability (HRV). As another example, the real-time gained recovery may be calculated as an overall score, where deeper sleep or higher quality sleep is weighted more greatly than lighter sleep or lower quality sleep. As such, an overall real-time gained recovery score may be calculated.

In operation 208, apparatus 25 may include means, such as the processor 20, user interface 22, or the like, for comparing the real-time gained recovery to the determined sleep recovery need. In this regard, apparatus 25, such as the processor 20, may repeatedly or continually, such as on a repeated time interval (e.g., every 30 seconds) compare the real-time gained recovery to the determined sleep recovery need of the user. It will be appreciated that the sleep recovery need of the user may be considered the sleep recovery need determine in operation 200, or the sleep recovery need as determine in operation 200 and as adjusted in operation 204 based on the user input of operation 202.

In some examples, every time the real-time gained recovery is calculated, recalculated, or adjusted to reflect recent data processed by apparatus 25, a comparison of the real-time gained recovery to the sleep recovery need may be performed.

To perform the comparison, apparatus 25, such as the processor 20, may compare the accumulated amount of time of actual sleep attributed to cycles or sleep quality to an amount of time for the respective cycle or sleep quality as indicated by the sleep recovery need. In some examples, when the amount of time of sleep attributed to a particular sleep cycle (e.g., REM) or quality classification is reached, apparatus 25, such as the processor 20, may determine the real-time gained recovery satisfies the sleep recovery need. As another example, in an instance the overall score of the real-time gained recovery meets or exceeds an overall target score indicated by the sleep recovery need, apparatus 25, such as the processor 20, may determine the sleep recovery need is met.

As shown by operation 210, apparatus 25 may include means, such as the processor 20, user interface 22, communication interface 24, memory device 26, or the like, for, in response to determining that the real-time gained recovery satisfies the sleep recovery need, causing a wake-up alert to be provided via a user interface of a device. The wake-up alert may be any type of alarm, such as auditory, haptic (e.g., vibration), visual, and/or any combination thereof. In some examples, the wake-up alert may provide a gradual alarm to gently wake the user once the user is rested, according to the sleep recovery need of the user. In some embodiments, apparatus 25, such as the processor 20 and/or the user interface 22, may dynamically cause the wake-up alert to be provided only when the sleep recovery need is satisfied. As such, apparatus 25 may include means, such as the processor 20, user interface 22, communication interface 24, memory device 26, or the like, for, in response to determining that the real-time gained recovery does not satisfy the sleep recovery need, preventing a wake-up alert from being provided.

As such, an example embodiment enables a user to obtain an optimal amount of sleep calculated according to their personalized sleep recovery need and their actual real-time gained recovery. In this regard, some example embodiments may prevent users from over sleeping, or sleeping beyond what is needed for optimal recovery. Individuals who otherwise sleep beyond their recovery need, such as those relying on a predetermined or scheduled alarm, may waste valuable time sleeping, while the extra sleep provides no health benefit, and in some examples may actually be detrimental to one's health or ability to sleep in the future. Certain example embodiments may therefore generate additional productive hours in the user's life. Further, an example embodiment may prevent users from waking prematurely, such as based on a predetermined or scheduled alarm, and thus enable users to achieve optimal recovery as determined based on personal needs and real-time gained recovery.

In some examples, as shown by operation 212, apparatus 25 may include means, such as the processor 20, communication interface 24, memory device 26, or the like, for updating a sleep history record. For example, apparatus 25, such as the processor 20 and/or the memory device 26, may advantageously update the sleep history record of a user as the sleep data is detected and/or processed. As example embodiments are used on an ongoing or continual basis by the user, for example, the sleep recovery need of the user, as calculated by the apparatus 25, such as the processor 20, may be affected by more recently captured sleep data. For example, several days in which a sleep recovery need is not satisfied, may result in an increase in the sleep recovery need, such that a sleep debt is accumulated. In some examples, excessive rest and/or sleep may be achieved, and the apparatus 25 may cause the sleep recovery need to be decreased. Apparatus 25, such as the processor 20 and/or the memory device 26, may therefore update the sleep history record of the user, such as detected sleep data stored on memory device 26.

An example embodiment may be advantageously configured by a user to obtain optimal sleep while still awaking in time for important tasks or obligations. As an example, such as in a scenario in which a user needs to awake by a certain time, the apparatus 25 may enable a default predefined alarm to be set by the user. In some embodiments, the default alarm will only cause a wake-up alert to be provided via the user interface if the default alarm time is reached, and apparatus 25 has not caused a wake-up alert to be provided in response to determining the real-time gained recovery satisfies the sleep recovery need. However, if a wake-up alert is provided in response to determining the real-time gained recovery satisfies the sleep recovery need in advance of reaching the default alarm time, the default alarm may be automatically canceled in some embodiments (or, in other embodiments, the default alarm may remain active as a precaution in case the user falls back to sleep following the wake-up alert).

An example embodiment may be used to prevent overnapping and/or to ensure optimal recovery during napping. Some example embodiments may therefore be adopted for use in daytime napping. A sleep recovery need of a user may therefore be determined for a nap, and the real-time gain recovery may be calculated during the nap. In some examples, apparatus 25 may limit a nap to a predetermined time limit, such as 30 minutes after falling asleep or after the sleep event indication is received, for example, to ensure the user does not over nap and/or disrupt nighttime sleep and/or circadian rhythm.

As such, an example embodiment allows a user to strike a balance between obtaining an optimal sleep recovery and waking in time to meet the user's obligations and tasks. As an example, the user may configure a device such that on weekends, apparatus 25 only causes the dynamic wake-up alert to be provided once the sleep recovery need is satisfied, but on weekdays or workdays, the default alarm is triggered if the time is reached prior to sleep recovery need satisfaction, so that the user does not oversleep for work or other commitments. During times of illness or other physical needs, a user may configure a device such that apparatus 25 only causes the dynamic wake-up alert to be provided once the sleep recovery need is satisfied. As another example, some example embodiments may help to ensure that commercial vehicle drivers, emergency responders, and/or the like achieve sufficient sleep recovery before returning to work. This example embodiment therefore promotes healthy sleep habits and well-being, as well as ensuring the safety of others.

In an example embodiment, apparatus 25 and/or any of the operations described herein, such as operation 200, may be utilized to monitor physical, for example, recovery after exercise. In this regard, an example embodiment may provide an alert or notification when a person is recovered (e.g., 100% recovered, or a portion thereof) and ready for a new physical exercise. The alert or notice may therefore also be provided when the person is awake. Further, in some use cases, it not be based on sleep data and/or a sleep recovery need, but rather a personalized physical recovery need indicating the user's recovery need from physical activity.

As described above, FIG. 2 illustrates a flowchart of an apparatus 25, method, and computer program product according to example embodiments of the invention. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory device 26 of an apparatus 25 employing an embodiment of the present invention and executed by a processor 20 of the apparatus 25. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, may be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the processor, cause the apparatus to at least:
   determine a sleep recovery need of a user;
   receive a desired recovery that the user desires to achieve, the desired recovery being a ratio of the determined sleep recovery need;
   adjust the determined sleep recovery need of the user based on the desired recovery;
   process sleep data collected via at least one sensor to monitor sleep recovery relating to the user and to calculate, in real-time, a gained recovery; and
   in response to determining that the gained recovery satisfies the adjusted sleep recovery need, cause a wake-up alert to be provided to the user via a user interface.

2. The apparatus according to claim 1, wherein the sleep recovery need is determined based on a mental stress level of the user.

3. The apparatus according to claim 1, wherein the sleep recovery need is determined based on physical activities of the user.

4. The apparatus according to claim 1, wherein the sleep recovery need is determined based on a sleep history record relating to the user.

5. The apparatus according to claim 1, wherein the sleep data is indicative of a quality of sleep.

6. The apparatus according to claim 1, wherein the sleep data is indicative of an amount of sleep.

7. The apparatus according to claim 1, wherein the gained recovery is calculated on a repeated time interval.

8. The apparatus according to claim 1, wherein the gained recovery is calculated in a repeated or continual manner.

9. A method comprising:
   determining a sleep recovery need of a user;
   receiving a desired recovery that the user desires to achieve, the desired recovery being a ratio of the determined sleep recovery need;
   adjusting the determined sleep recovery need of the user based on the desired recovery;
   processing sleep data collected via at least one sensor to monitor sleep recovery relating to the user and to calculate, in real-time, a gained recovery; and
   in response to determining that the gained recovery satisfies the adjusted sleep recovery need, causing a wake-up alert to be provided to the user via a user interface.

10. The method according to claim 9, wherein the determined sleep recovery need is determined based on a mental stress level of the user.

11. The method according to claim 9, wherein the determined sleep recovery need is determined based on physical activities of the user.

12. The method according to claim 9, wherein the determined sleep recovery need is determined based on a sleep history record relating to the user.

13. The method according to claim 9, wherein the sleep data is indicative of a quality of sleep.

14. The method according to claim 9, wherein the sleep data is indicative of an amount of sleep.

15. The method according to claim 9, wherein the gained recovery is calculated on a repeated time interval.

16. The method according to claim 9, wherein the gained recovery is calculated in a repeated or continual manner.

17. A computer program product comprising at least one non-transitory computer-readable storage medium having computer-executable program code instructions stored therein, the computer-executable program code instructions comprising program code instructions to at least:
   determine a sleep recovery need of a user;
   receive a desired recovery that the user desires to achieve, the desired recovery being a ratio of the determined sleep recovery need;
   adjust the determined sleep recovery need of the user based on the desired recovery;
   process sleep data collected via at least one sensor to monitor sleep recovery relating to the user and to calculate, in real-time, a gained recovery; and
   in response to a determining that the gained recovery satisfies the adjusted sleep recovery need, cause a wake-up alert to be provided to the user via a user interface.

18. The computer program product according to claim 17, wherein the gained recovery is calculated on a repeated time interval.

19. The computer program product according to claim 17, wherein the gained recovery is calculated in a repeated or continual manner.

* * * * *